US012700477B2

(12) United States Patent
Beal

(10) Patent No.: US 12,700,477 B2
(45) Date of Patent: Aug. 4, 2026

(54) GENERATING SUBSEQUENCE CATALOGS FOR NUCLEIC ACID SYNTHESIS

(71) Applicant: RTX BBN Technologies, Inc., Cambridge, MA (US)

(72) Inventor: Jacob Stuart Michael Beal, Iowa City, IA (US)

(73) Assignee: RTX BBN Technologies, Inc., Cambridge, MA (US)

( * ) Notice: Subject to any disclaimer, the term of this patent is extended or adjusted under 35 U.S.C. 154(b) by 990 days.

(21) Appl. No.: 17/232,749

(22) Filed: Apr. 16, 2021

(65) Prior Publication Data

US 2021/0327539 A1      Oct. 21, 2021

Related U.S. Application Data

(60) Provisional application No. 63/011,700, filed on Apr. 17, 2020.

(51) Int. Cl.

| | |
|---|---|
| *G16B 30/20* | (2019.01) |
| *C12N 15/10* | (2006.01) |
| *G16B 35/10* | (2019.01) |
| *G16B 40/00* | (2019.01) |
| *G16B 50/50* | (2019.01) |

(52) U.S. Cl.
CPC ......... *G16B 30/20* (2019.02); *C12N 15/1089* (2013.01); *G16B 35/10* (2019.02); *G16B 40/00* (2019.02); *G16B 50/50* (2019.02)

(58) Field of Classification Search
CPC .... C12N 15/1089; G16B 35/10; G16B 40/00; G16B 50/50
See application file for complete search history.

(56) References Cited

U.S. PATENT DOCUMENTS

| | | | | |
|---|---|---|---|---|
| 2017/0147748 | A1* | 5/2017 | Staehler | G16B 50/00 |
| 2018/0362969 | A1* | 12/2018 | Banal | C12N 15/1068 |
| 2020/0299684 | A1* | 9/2020 | Toro | G16B 30/20 |
| 2020/0357483 | A1* | 11/2020 | Roquet | G16B 50/50 |

OTHER PUBLICATIONS

Ceze, L., Nivala, J. and Strauss, K. Molecular digital data storage using DNA. Nature Reviews Genetics, 20(8), pp. 456-466. (Year: 2019).*
Linshiz, G., Yehezkel, T.B., Kaplan, S., Gronau, I., Ravid, S., Adar, R. and Shapiro, E. Recursive construction of perfect DNA molecules from imperfect oligonucleotides. Molecular Systems Biology, 4(1), p. 1-10. (Year: 2008).*
Lozano, M., Rodriguez, F.J. and García-Martínez, C. A two-stage constructive method for the unweighted minimum string cover problem. Knowledge-Based Systems, 77, pp. 103-113. (Year: 2015).*
Blawat, M. et al.; "Forward Error Correction for DNA Data Storage"; Procedia Computer Science, vol. 80; pp. 1011-1022 (2016).
Bornholt, J. et al.; "A Dna-Based Archival Storage System"; ASPLOS Conference; Atlanta, GA (2016).
Carr, S. et al.; "Reducing DNA context dependence in bacterial promoters"; PLoS One, vol. 12, Issue No. 4, e0176013 (2017).
Church, G. et al.; "Next-Generation Digital Information Storage in DNA"; Science, vol. 337, Issue No. 6102: 1628 (2012).
Erlich, Y. et al.; "DNA Fountain enables a robust and efficient storage architecture"; Science, vol. 355; pp. 950-954 (2017).
Goldman, N. et al.; "Towards practical, high-capacity, low-maintenance information storage in synthesized DNA"; Nature, vol. 494, Issue No. 7435; pp. 77-80 (2013) DOI: 10.1038/nature11875.
Skinner, G. et al.; "Biocompatible Writing of Data into DNA"; Journal of Bionanoscience, vol. 1; pp. 17-21 (2007).

* cited by examiner

*Primary Examiner* — Olivia M. Wise
*Assistant Examiner* — Janna Nicole Schultzhaus
(74) *Attorney, Agent, or Firm* — Schwegman Lundberg & Woessner, P.A.

(57)      ABSTRACT

Techniques for generating custom libraries for nucleic acid synthesis are disclosed. The techniques include: obtaining one or more nucleic acid sequences for which to generate a subsequence catalog; performing pattern recognition on the one or more nucleic acid sequences, to identify subsequences that are repeated in the one or more nucleic acid sequences; and generating the subsequence catalog, including the subsequences that are repeated in the one or more nucleic acid sequences.

14 Claims, 4 Drawing Sheets

Specification includes a Sequence Listing.

System 100

GENERATING SUBSEQUENCE CATALOGS FOR NUCLEIC ACID SYNTHESIS

RELATED APPLICATIONS

This application claims the benefit of U.S. Provisional Patent Application Ser. No. 63/011,700, titled "CUSTOM LIBRARIES FOR ACCELERATED MICROFLUIDIC NUCLEIC ACID SYNTHESIS," filed Apr. 17, 2020, which is hereby incorporated by reference in its entirety.

SEQUENCE LISTING

The instant application contains a Sequence Listing which has been submitted electronically in ST25 compliant .TXT format and is hereby incorporated by reference in its entirety. Said .TXT file, created on May 8, 2024, is named 3547063US1.xml and is approximately 4,096 bytes in size. The content of the .TXT file compliant with the ST25 format and incorporated herein by reference is a computer readable form (CRF) of two (2) sequences:

SEQ ID NO:1 is an example of a repeated nucleic acid sequence provided for the purposes of demonstration.

SEQ ID NO:2 is a second example of a repeated nucleic acid sequence provided for the purposes of demonstration.

BACKGROUND

Nucleic acid synthesis is a key bottleneck in many area of modem biotechnology. The time to synthesize a sequence may be on the order of days or weeks per sequence. One reason for the bottleneck is that synthesis is typically conducted one base at a time. A synthesis system stores copies of each individual base and joins the appropriate base at each step in the desired sequence, which is a very slow process. In addition, because each joining reaction carries some risk of error and error accumulates exponentially with each reaction in the process, every additional base in the desired sequence increases the accumulated risk associated with synthesizing that sequence.

Approaches described in this section have not necessarily been conceived and/or pursued prior to the filing of this application. Accordingly, unless otherwise indicated, approaches described in this section should not be construed as prior art.

TECHNICAL FIELD

The present disclosure relates generally to nucleic acid synthesis.

SUMMARY

In general, in one aspect, one or more non-transitory computer-readable media store instructions that, when executed by one or more processors, cause the one or more processors to perform operations including: obtaining one or more nucleic acid sequences for which to generate a subsequence catalog; performing pattern recognition on the one or more nucleic acid sequences, to identify subsequences that are repeated in the one or more nucleic acid sequences; and generating the subsequence catalog, including the subsequences that are repeated in the one or more nucleic acid sequences.

The operations may further include: assembling a fragment library, including nucleic acid fragments corresponding to the subsequences in the subsequence catalog; and synthesizing a desired nucleic acid sequence using the fragment library. Assembling the fragment library may be performed concurrently with synthesizing the desired nucleic acid sequence.

The operations may further include: determining that at least one subsequence in the subsequences does not satisfy an inclusion criterion for the subsequence catalog; and responsive to determining that the at least one subsequence does not satisfy the inclusion criterion, excluding the at least one subsequence from the subsequence catalog.

Performing pattern recognition on the one or more nucleic acid sequences may include: applying a compression algorithm to the one or more nucleic acid sequences; and identifying the subsequences as those used by the compression algorithm to reduce a size of the one or more nucleic acid sequences.

The one or more nucleic acid sequences may include sequences in a particular category of nucleic acid sequences and the subsequence catalog may be for sequencing members of the particular category of nucleic acid sequences.

The subsequence catalog may be for a nucleic acid data storage system.

In general, in another aspect, a system includes at least one device including a hardware processor. The at least one device is configured to perform operations including: obtaining one or more nucleic acid sequences for which to generate a subsequence catalog; performing pattern recognition on the one or more nucleic acid sequences, to identify subsequences that are repeated in the one or more nucleic acid sequences; and generating the subsequence catalog, including the subsequences that are repeated in the one or more nucleic acid sequences.

The operations may further include: assembling a fragment library, including nucleic acid fragments corresponding to the subsequences in the subsequence catalog; and synthesizing a desired nucleic acid sequence using the fragment library. Assembling the fragment library may be performed concurrently with synthesizing the desired nucleic acid sequence.

The operations may further include: determining that at least one subsequence in the subsequences does not satisfy an inclusion criterion for the subsequence catalog; and responsive to determining that the at least one subsequence does not satisfy the inclusion criterion, excluding the at least one subsequence from the subsequence catalog.

Performing pattern recognition on the one or more nucleic acid sequences may include: applying a compression algorithm to the one or more nucleic acid sequences; and identifying the subsequences as those used by the compression algorithm to reduce a size of the one or more nucleic acid sequences.

The one or more nucleic acid sequences may include sequences in a particular category of nucleic acid sequences and the subsequence catalog may be for sequencing members of the particular category of nucleic acid sequences.

The subsequence catalog may be for a nucleic acid data storage system.

In general, in another aspect, a method includes: obtaining one or more nucleic acid sequences for which to generate a subsequence catalog; performing pattern recognition on the one or more nucleic acid sequences, to identify subsequences that are repeated in the one or more nucleic acid sequences; and generating the subsequence catalog, including the subsequences that are repeated in the one or more nucleic acid sequences.

The method may further include: assembling a fragment library, including nucleic acid fragments corresponding to the subsequences in the subsequence catalog; and synthesizing a desired nucleic acid sequence using the fragment library. Assembling the fragment library may be performed concurrently with synthesizing the desired nucleic acid sequence.

The method may further include: determining that at least one subsequence in the subsequences does not satisfy an inclusion criterion for the subsequence catalog; and responsive to determining that the at least one subsequence does not satisfy the inclusion criterion, excluding the at least one subsequence from the subsequence catalog.

Performing pattern recognition on the one or more nucleic acid sequences may include: applying a compression algorithm to the one or more nucleic acid sequences; and identifying the subsequences as those used by the compression algorithm to reduce a size of the one or more nucleic acid sequences.

The one or more nucleic acid sequences may include sequences in a particular category of nucleic acid sequences and the subsequence catalog may be for sequencing members of the particular category of nucleic acid sequences.

The subsequence catalog may be for a nucleic acid data storage system.

One or more embodiments described in this Specification and/or recited in the claims may not be included in this General Overview section.

BRIEF DESCRIPTION OF THE DRAWINGS

Various aspects of at least one embodiment are discussed below with reference to the accompanying Figures, which are not intended to be drawn to scale. The Figures are included to provide illustration and a further understanding of the various aspects and embodiments, and are incorporated in and constitute a part of this specification, but are not intended to define the limits of the disclosure. In the Figures, each identical or nearly identical component that is illustrated in various Figures is represented by a like numeral. For the purposes of clarity, some components may not be labeled in every figure. In the Figures.

DETAILED DESCRIPTION

1. System Architecture

As used herein, the term "nucleic acid sequence," or simply "sequence," refers to a deoxyribonucleic acid (DNA) sequence, a ribonucleic acid (RNA) sequence, a synthetic nucleic acid sequence, or any other kind of nucleic acid sequence. A sequence may be a subset of a larger sequence. For example, a sequence may include a subset of an organism's genome. The term "subsequence," also referred to herein as a "fragment," refers to a subset of a particular sequence of interest. Given a sequence of length n, excluding the entire n-length sequence, there are $$\frac{n(n+1)}{2} - 1$$

subsequences. In a given sequence, some subsequences may be repeated. For example, in the sequence identified as SEQ. ID. NO:1, AATACATAA, the subsequences A, AA, AT, ATA, and TA are repeated. Embodiments described herein take advantage of the existence of multi-base repeating subsequences (e.g., AA, AT, ATA, and TA in the preceding example) to generate a subsequence catalog that allows for more efficient sequencing of nucleic acid sequences than if those sequences were entirely synthesized one base at a time.

Figure 1:
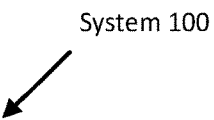
FIG. 1 is a block diagram of an example of a system according to an embodiment.
Figure 1:
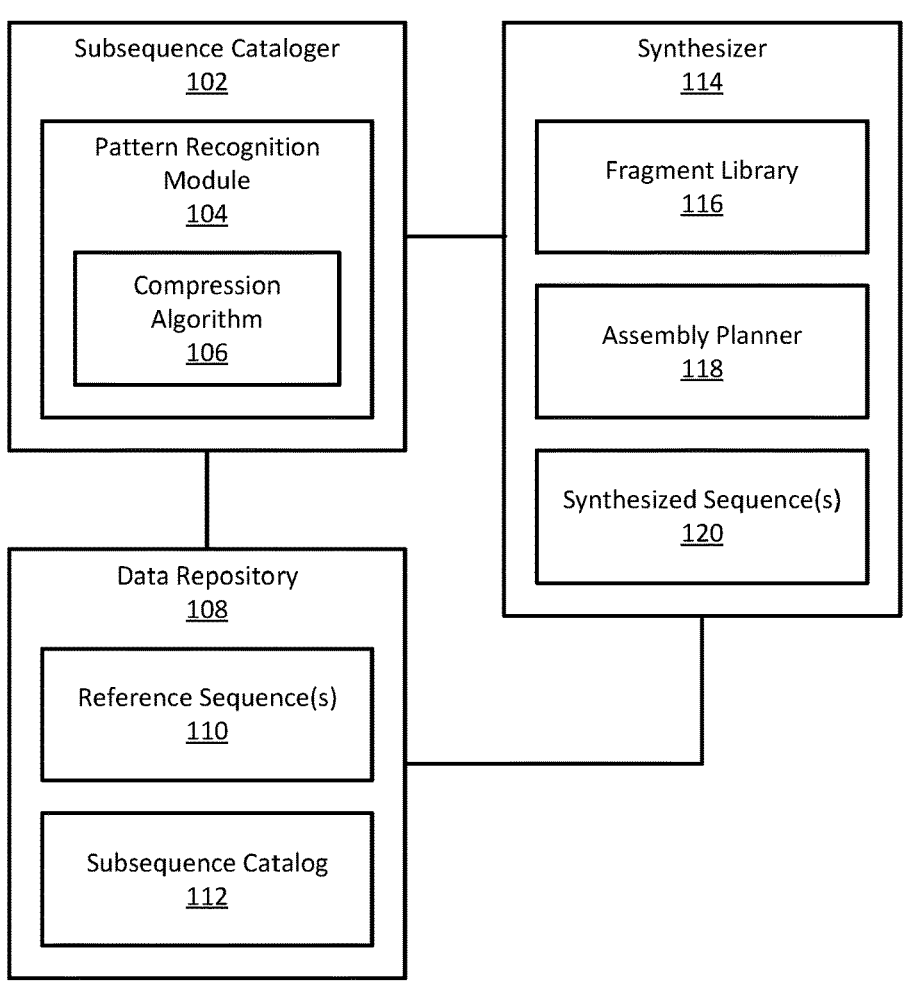

FIG. 1 is a block diagram of an example of a system 100 according to an embodiment. In an embodiment, the system 100 may include more or fewer components than the components illustrated in FIG. 1. The components illustrated in FIG. 1 may be local to or remote from each other. The components illustrated in FIG. 1 may be implemented in software and/or hardware. Each component may be distributed over multiple applications and/or machines. Multiple components may be combined into one application and/or machine. Operations described with respect to one component may instead be performed by another component.

As illustrated in FIG. 1, the system 100 includes a subsequence cataloger 102. The subsequence cataloger 102 is a set of hardware, software, and/or firmware configured to perform operations for generating a subsequence catalog 112. Examples of operations for generating a subsequence catalog 112 are described herein. The subsequence cataloger 102 includes a pattern recognition module 104 configured to perform operations described herein for recognizing patterns in reference sequence(s) 110, i.e., subsequences that are repeated within the reference sequence(s) 110. For example, the pattern recognition module 104 may be configured to execute a compression algorithm 106 on the reference sequence(s) 110, to identify subsequences that are repeated in the reference sequence(s) 110. Some or all repeated subsequences that are candidates for compression may also be suitable for inclusion in the subsequence catalog 112.

The reference sequence(s) 110 include(s) one or more sequences that the subsequence cataloger 102 uses to generate the subsequence catalog 112. If the subsequence catalog 112 is intended to be used for synthesizing a single sequence that is known in advance, the reference sequence (s) 110 may include only that single sequence. Alternatively, the subsequence catalog 112 may be intended for synthesizing sequences of a particular type (e.g., family, genus, species, or other type), and the reference sequence(s) 110 may include two or more non-identical sequences of that type. Due to similarities in repeating subsequences among non-identical sequences of the same type, the resulting subsequence catalog 112 may thus allow for more efficient synthesis of sequences of that type, even if the specific sequence to be synthesized is not one of the reference sequence(s) 110. Alternatively, the subsequence catalog 112 may be intended for "generic" or general-use synthesis, and the reference sequence(s) 110 may include a sampling of sequences of multiple types. Due to similarities in repeating subsequences even across different sequence types, the resulting subsequence catalog 112 may thus allow for more efficient synthesis generally.

As non-limiting examples:

1. There is considerable diversity in the population of *Escherichia coli* (*E. coli*) bacteria. The reference sequence(s) 110 may include multiple non-identical *E. coli* sequences, so that the resulting subsequence catalog 112 allows for more efficient synthesis of *E. coli* sequences generally.

2. Multiple variants of severe acute respiratory syndrome coronavirus 2 (SARS-CoV-2) exist. The reference sequence(s) 110 may include multiple non-identical SARS-CoV-2 sequences, so that the resulting subsequence catalog 112 allows for more efficient synthesis of SARS-CoV-2 sequences generally.

3. Clustered regularly interspaced short palindromic repeats (CRISPR) refers to a family of nucleic acid sequences found in a large percentage of bacteria and archaea. The reference sequence(s) 110 may include multiple non-identical CRISPR sequences, so that the resulting subsequence catalog 112 allows for more efficient synthesis in CRISPR systems generally. Techniques described herein may be used to generate a subsequence catalog 112 for synthesizing guide RNA (gRNA) and/or single guide RNA (sgRNA) to be used in CRISPR systems.

4. Medical diagnostics often require a minimum amount of the particular nucleic acid sequence to be tested. However, an insufficiently large sample of the sequence to be tested may be provided. The reference sequence (s) 110 may include the sample sequence, so that the resulting subsequence catalog 112 allows for more efficient synthesis of enough copies of the sequence to be tested.

In general, greater similarity among the reference sequence(s) 110 allows for more efficient synthesis of identical or very similar sequences, while more variety among the reference sequence(s) 110 allows for broader applicability at the expense of some efficiency. If the reference sequence(s) 110 include only a single sequence, the resulting subsequence catalog 112 allows for very efficient synthesis of that particular sequence. If the reference sequence(s) include non-identical sequences of the same type, the subsequence catalog 112 allows for more efficient synthesis of sequences of that type, but may be less efficient for a specific sequence than if the reference sequence(s) 110 had been more narrowly tailored to that specific sequence.

The system 100 may include a synthesizer 114. A synthesizer 114 includes hardware for joining subsequences of bases to generate one or more synthesized sequence(s) 120. The synthesizer 114 may further include one or more processors, along with software and/or firmware configured to direct the operation of sequence synthesis. The synthesizer 114 is configured to use a fragment library 116, also referred to as a microfluidic library. The fragment library 116 includes physical copies of the subsequences to be used for synthesizing one or more sequences. The synthesizer 114 may be configured to build some or all of the fragment library 116 based on a subsequence catalog 112. Alternatively or additionally, the synthesizer 114 may be configured to receive some or all of the fragment library 116 preassembled from another source.

The synthesizer 114 may include an assembly planner 118. An assembly planner 118 includes hardware, software, and/or firmware configured to determine, given one or more target sequences and a fragment library 116, how to assemble subsequences (or "fragments") from the fragment library 116 to generate the synthesized sequence(s) 120. The assembly planner 118 may reference the subsequence catalog 112 for knowledge of what fragments are available in the fragment library 116.

The assembly planner 118 may use various techniques to determine which fragments to use, and in which order. In one possible heuristic (referred to in the example below as heuristic A), the assembly planner 118 may start with the longest subsequence in the fragment library 116 and determine where it matches the target sequence; those locations are now accounted for. The assembly planner 118 may then do the same for the next-longest fragment and the remaining portions of the target sequence, and so on, until all locations of the target sequence are accounted for by fragments in the fragment library 116. The assembly planner 118 may then perform synthesis using the actual fragments in that order. In another possible heuristic (referred to in the example below as heuristic B), the assembly planner 118 may start with the first base in a sequence and find the longest subsequence in the fragment library 116 that matches the beginning of the sequence, then move to the next portion of the sequence and find the longest subsequence that matches starting at that position, and so on.

For example, given a sequence, identified as SEQ. ID. NO:2, ACTGACCAATGCA and a library of {TGAC, ACT, GAC, AAT, AATG, A, C, T, G}, heuristics A and B would result in the following coverage:

```
Heuristic A: A-C-TGAC-C-AATG-C-A

Heuristic B: ACT-GAC-C-AATG-C-A
```

Alternatively, the assembly planner 118 may use another heuristic or optimization approach to apply the fragments from the fragment library 116 to synthesis of the target sequence.

In an embodiment, a data repository 108 is any type of storage unit and/or device (e.g., a file system, database, collection of tables, or any other storage mechanism) for storing data. For example, as illustrated in FIG. 1, a data repository 108 may store one or more reference sequence(s) 110 and/or a subsequence catalog 112. A data repository 108 may include multiple different storage units and/or devices. The multiple different storage units and/or devices may or may not be of the same type or located at the same physical site. Further, a data repository 108 may be implemented or may execute on the same computing system as one or more other components of the system 100. Alternatively or additionally, a data repository 108 may be implemented or executed on a computing system separate from one or more other components of the system 100. A data repository 108 may be logically integrated with one or more other components of the system 100. Alternatively or additionally, a data repository 108 may be communicatively coupled to one or more other components of the system 100 via a direct connection or via a network. In FIG. 1, a data repository 108 is illustrated as storing various kinds of information. Some or all of this information may be implemented and/or distributed across any of the components of the system 100. However, this information is illustrated within the data repository 108 for purposes of clarity and explanation.

In an embodiment, one or more components of the system 100 are implemented on one or more digital devices. The term "digital device" generally refers to any hardware device that includes a processor. A digital device may refer to a physical device executing an application or a virtual machine. Examples of digital devices include a computer, a tablet, a laptop, a desktop, a netbook, a server, a web server, a network policy server, a proxy server, a generic machine, a function-specific hardware device, a hardware router, a hardware switch, a hardware firewall, a hardware network address translator (NAT), a hardware load balancer, a mainframe, a television, a content receiver, a set-top box, a printer, a mobile handset, a smartphone, a personal digital assistant ("PDA"), a wireless receiver and/or transmitter, a base station, a communication management device, a router, a switch, a controller, an access point, and/or a client device.

2. Operations for Generating a Subsequence Catalog

Figure 2:
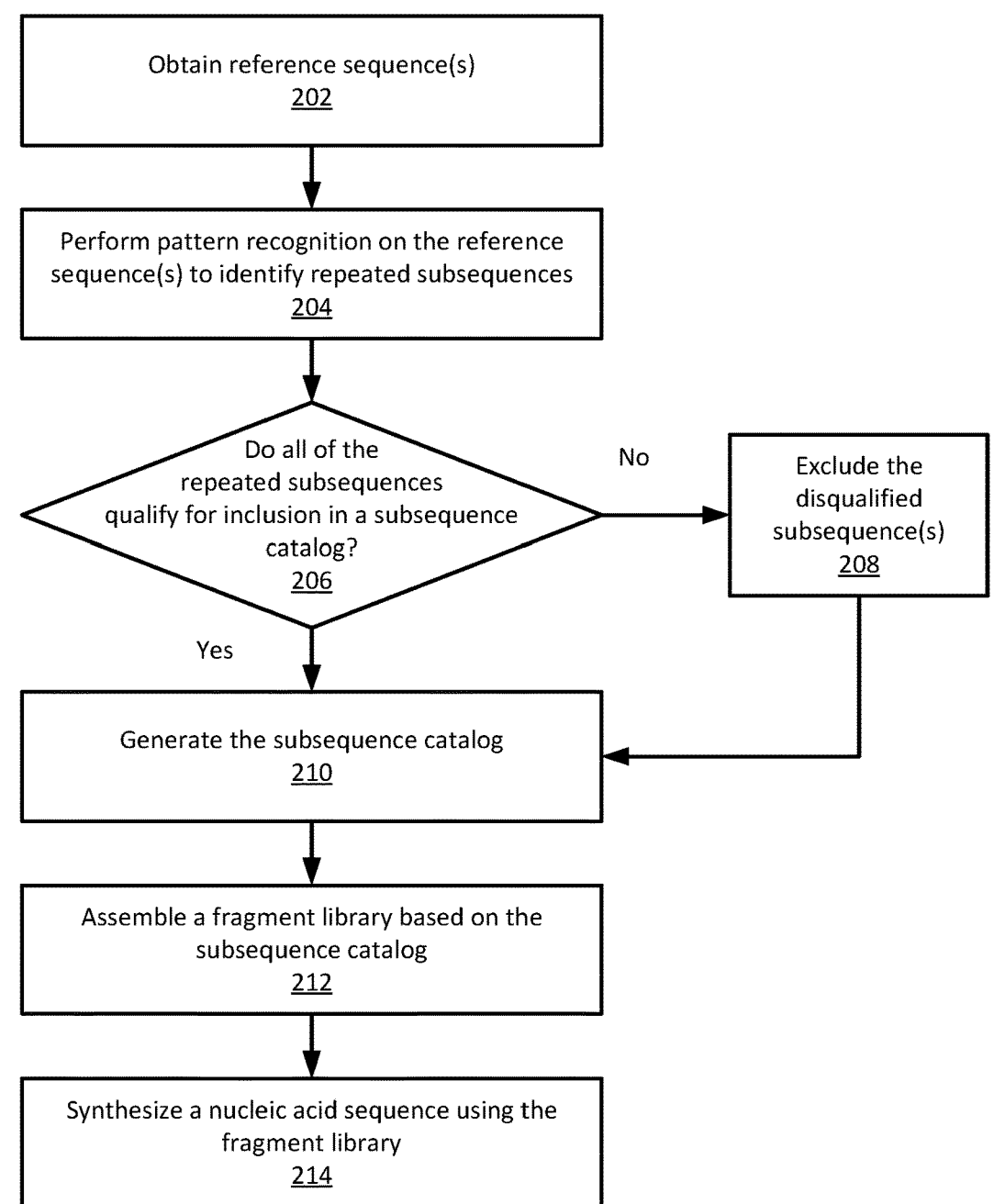
FIG. 2 is a flow diagram of an example of operations for generating a subsequence catalog for nucleic acid synthesis according to an embodiment.

FIG. 2 is a flow diagram of an example of operations for generating a subsequence catalog for nucleic acid synthesis according to an embodiment according to an embodiment. One or more operations illustrated in FIG. 2 may be modified, rearranged, or omitted all together. Accordingly, the particular sequence of operations illustrated in FIG. 2 should not be construed as limiting the scope of one or more embodiments.

As discussed above with reference to FIG. 1, generating a subsequence catalog is based on one or more reference sequences. A subsequence cataloger obtains the reference sequence(s) (Operation 202) to use for generating the subsequence catalog. The subsequence cataloger may obtain the reference sequence(s) from a local or remote database, by sequencing one or more molecules, and/or from another source. The reference sequence(s) may include a single sequence, two or more sequences of the same type, and/or two or more sequences of different types.

The subsequence cataloger performs pattern recognition on the reference sequence(s) to identify repeated subsequences (Operation 204). Pattern recognition may be performed in various ways. In general, pattern recognition analyzes one or more sequences to identify subsequences that occur more than once. Pattern recognition may be configured to identify subsequences that occur at least a threshold number of times, or a certain number or percentage of subsequences that repeat most frequently. Alternatively or additionally, pattern recognition may be configured to identify repeating subsequences of at least a minimum number of bases.

As discussed above, pattern recognition may use a compression algorithm. Specifically, pattern recognition may use a compression algorithm that identifies repeating strings of data in the data set. For example, pattern recognition may apply the Lempel-Ziv-Welch (LZW) compression algorithm to the reference sequence(s). The subsequence cataloger may consider some or all of the dictionary entries produced by the LZW coding (or other compression algorithm that identifies repeating subsequences) as candidates for inclusion in a subsequence catalog.

In an embodiment, not all repeating subsequences qualify for inclusion in the subsequence catalog. Inclusion criteria may include, for example: subsequences that are repeated least a threshold number of times; a subset of subsequences (e.g., a predetermined threshold number or percentage of repeated subsequences) that repeat most frequently; repeating subsequences of at least a minimum number of bases; and/or subsequences that are not expected to exceed a threshold error rate during synthesis. For each repeated subsequence, the subsequence cataloger may determine whether the repeated subsequence qualifies for inclusion in the subsequence catalog (Operation 206). If a repeated subsequence does not qualify for inclusion in the subsequence catalog, then the sequence cataloger excludes the disqualified subsequence from the subsequence catalog (Operation 208).

The subsequence cataloger generates the subsequence catalog (Operation 210) to include the repeated subsequences, optionally excluding repeated subsequences that do not satisfy one or more inclusion criteria. The subsequence catalog may also include single bases. Alternatively or additionally, the subsequence catalog may include information based on frequencies of repeated subsequences in the reference sequence(s).

In an embodiments, techniques for generating the subsequence catalog may be applied iteratively. The subsequence catalog may itself include repeating patterns or "motifs." Such motifs may appear when working with proteins, for example. For example, a subsequence in the catalog may be 20 bases long but share a 10-base fragment with another subsequence. As another example, a given subsequence may include the same pattern of bases repeated two or more times. A second-order subsequence catalog may be generated for building a fragment library based on the first-order subsequence catalog. Similarly, a third-order subsequence catalog may be generated for building fragments corresponding to the second-order subsequence catalog, and so on. Applying these techniques iteratively may thus help accelerate the process of building a fragment library.

A fragment library may be assembled based on the subsequence catalog (Operation 212), by the subsequence cataloger, a synthesizer, and/or another component. If the subsequence catalog includes information based on subsequence frequencies, the fragment library may include more inventory of subsequences that were determined to occur more frequently in the reference sequence(s). Thus, one or more embodiments help improve efficiency of material expenditures when synthesizing sequences, by helping to avoid overproduction of subsequences that are used less frequently than others.

A synthesizer may use the fragment library to synthesize a nucleic acid sequence (Operation 214). The sequence to be synthesized may be identical to a reference sequence used to generate the subsequence catalog, or may be a different subsequence. A synthesizer using a fragment library that includes repeated subsequences can perform more efficiently than a synthesizer that only joins single bases. For example, if synthesis joins an average of two bases per operation, synthesis will be roughly twice as fast as if synthesis only joined a single base at a time. In some cases, based on observed compression ratios of nucleic acid sequences, performance may be on the order of ten times better. In addition, using longer subsequences reduces the number of reactions needed, thus reducing the cumulative error associated with the reactions. Error rates may further be reduced by considering the expected error rates associated with particular subsequences, and including those subsequences that are less likely to produce errors during synthesis.

In an embodiment, the subsequence cataloger may be part of the synthesizer and may generate the subsequence catalog "online" or "on-the-fly," i.e., during synthesis. The synthesizer may begin with only a generic library, which may include only single bases and/or generic subsequences of length k. Upon receiving a target sequence, the synthesizer may use techniques described herein to generate a subsequence catalog for the target sequence, and then use the generic library to synthesize a fragment library for the target sequence. For example, the synthesizer may determine that the target sequence requires 10 copies of the fragment ACTG; the synthesizer may generate those 10 copies "on-the-fly," dispensing a copy when needed and holding the rest in reserve. On-the-fly generation of a fragment library takes longer than starting from a pre-prepared library, but also allows the synthesizer to generate custom fragment libraries for any target sequence encountered. The performance benefits of a custom fragment library may outweigh the start-up costs of online generation of that library.

An alternative to generating a custom library as described herein would be to generate a generic fragment library using all subsequences of length k. For example, for length 4, a fragment library may include AAAA, AAAC, AAAT, AACA, . . . , TTTT), plus single bases for completing sequences not divisible by k (e.g., the length 5 sequence ACTAA). However, this approach would be less efficient than identifying repeating subsequences in reference sequences. The sequences that people wish to synthesize typically are not evenly distributed, for reasons of both biochemistry and history/popularity. In addition, due to the inclusion of single bases, the completed library would be highly redundant, supporting a large number of ways in which the same sequence can be constructed (e.g., ACTAA as either A+CTAA or ACTA+A). It is more efficient, using techniques described herein, to consider the distribution of sequences to be created and reduce the number of redundant construction options. In addition, eliminating redundant construction options results in a smaller fragment library, thus reducing the material expense of synthesis.

3. Detailed Example

A detailed example (300) is described below with reference to FIG. 3, for purposes of clarity. Components and/or operations described below should be understood as examples that may not be applicable to one or more embodiments. Accordingly, components and/or operations described below should not be construed as limiting the scope of one or more embodiments.

Figure 3:
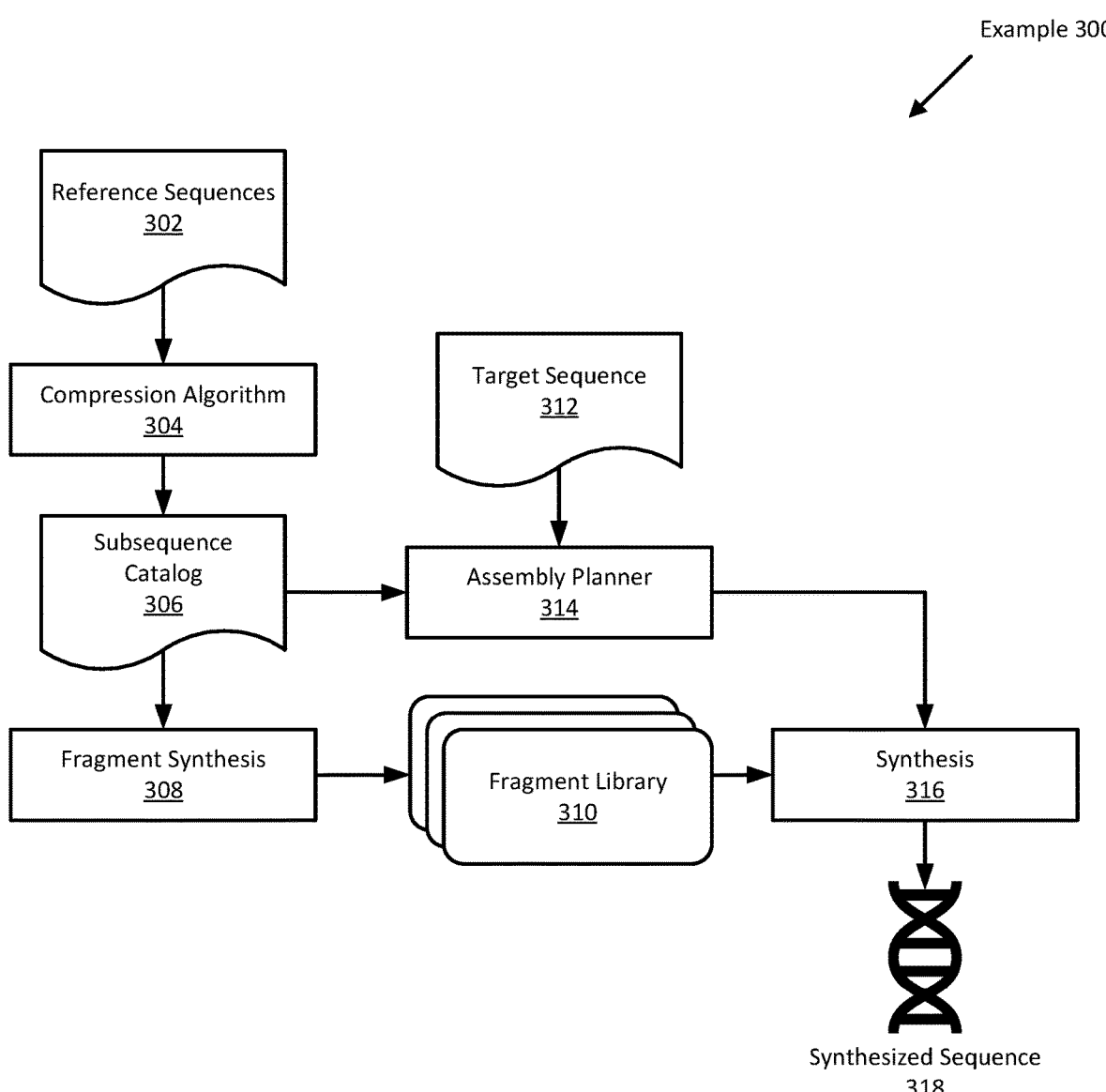
FIG. 3 is a block diagram of an example of generating a subsequence catalog for nucleic acid synthesis according to an embodiment.

As illustrated in FIG. 3, a compression algorithm 304 receives reference sequences 302 and generates a subsequence catalog 306. The subsequence catalog 308 is used as input to fragment synthesis 308, to generate a corresponding fragment library 310. Given a target sequence 312 and the subsequence catalog 306, an assembly planner 314 determines how to synthesize the target sequence 312 using the fragments available in the fragment library 310. The assembly planner 314 then directs synthesis 316 of those fragments into the synthesized sequence 318.

4. General; Computer Systems; Networks

In an embodiment, a system includes one or more devices, including one or more hardware processors, that are configured to perform any of the operations described herein and/or recited in any of the claims.

In an embodiment, one or more non-transitory computer-readable storage media store instructions that, when executed by one or more hardware processors, cause performance of any of the operations described herein and/or recited in any of the claims.

Any combination of the features and functionalities described herein may be used in accordance with an embodiment. In the foregoing specification, embodiments have been described with reference to numerous specific details that may vary from implementation to implementation. Accordingly, the specification and figures are to be regarded in an illustrative rather than a restrictive sense. The sole and exclusive indicator of the scope of the invention, and what is intended by the Applicant to be the scope of the invention, is the literal and equivalent scope of the set of claims that issue from this application, in the specific form in which such claims issue, including any subsequent correction.

In an embodiment, techniques described herein are implemented by one or more special-purpose computing devices (i.e., computing devices specially configured to perform certain functionality). The special-purpose computing device(s) may be hard-wired to perform the techniques and/or may include digital electronic devices such as one or more application-specific integrated circuits (ASICs), field programmable gate arrays (FPGAs), and/or network processing units (NPUs) that are persistently programmed to perform the techniques. Alternatively or additionally, a computing device may include one or more general-purpose hardware processors programmed to perform the techniques pursuant to program instructions in firmware, memory, and/or other storage. Alternatively or additionally, a special-purpose computing device may combine custom hard-wired logic, ASICs, FPGAs, or NPUs with custom programming to accomplish the techniques. A special-purpose computing device may include a desktop computer system, portable computer system, handheld device, networking device, and/or any other device(s) incorporating hard-wired and/or program logic to implement the techniques.

Figure 4:
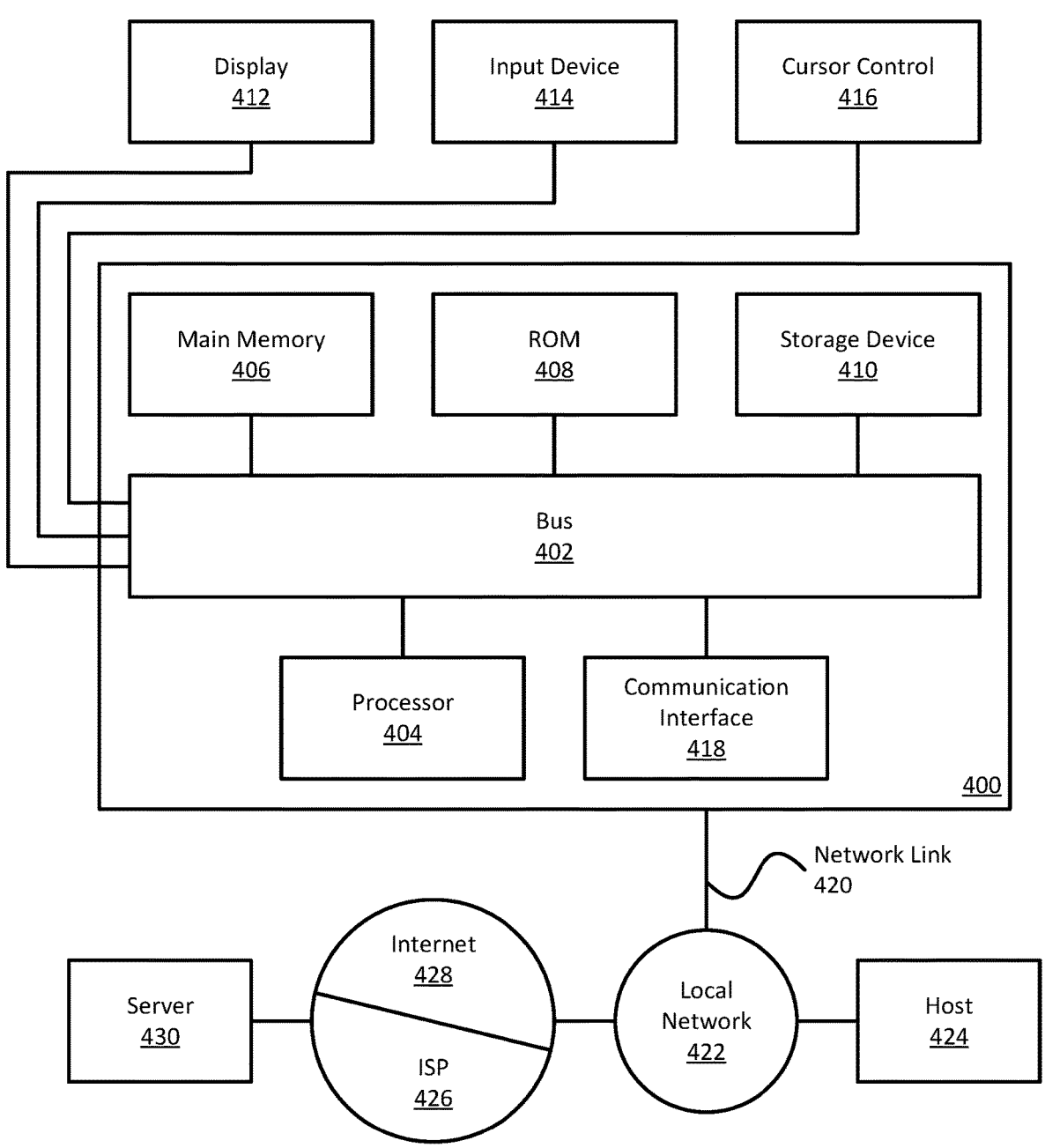
FIG. 4 is a block diagram of an example of a computer system according to an embodiment.

For example, FIG. 4 is a block diagram of an example of a computer system 400 according to an embodiment. Computer system 400 includes a bus 402 or other communication mechanism for communicating information, and a hardware processor 404 coupled with the bus 402 for processing information. Hardware processor 404 may be a general-purpose microprocessor.

Computer system 400 also includes a main memory 406, such as a random access memory (RAM) or other dynamic storage device, coupled to bus 402 for storing information and instructions to be executed by processor 404. Main memory 406 also may be used for storing temporary variables or other intermediate information during execution of instructions to be executed by processor 404. Such instructions, when stored in one or more non-transitory storage media accessible to processor 404, render computer system 400 into a special-purpose machine that is customized to perform the operations specified in the instructions.

Computer system 400 further includes a read only memory (ROM) 408 or other static storage device coupled to bus 402 for storing static information and instructions for processor 404. A storage device 410, such as a magnetic disk or optical disk, is provided and coupled to bus 402 for storing information and instructions.

Computer system 400 may be coupled via bus 402 to a display 412, such as a liquid crystal display (LCD), plasma display, electronic ink display, cathode ray tube (CRT) monitor, or any other kind of device for displaying information to a computer user. An input device 414, including alphanumeric and other keys, may be coupled to bus 402 for communicating information and command selections to processor 404. Alternatively or additionally, computer system 400 may receive user input via a cursor control 416, such as a mouse, a trackball, a trackpad, or cursor direction keys for communicating direction information and command selections to processor 404 and for controlling cursor movement on display 412. This input device typically has two degrees of freedom in two axes, a first axis (e.g., x) and a second axis (e.g., y), that allows the device to specify positions in a plane. Alternatively or additionally, computer system 4 may include a touchscreen. Display 412 may be configured to receive user input via one or more pressure-sensitive sensors, multi-touch sensors, and/or gesture sensors. Alternatively or additionally, computer system 400 may receive user input via a microphone, video camera, and/or some other kind of user input device (not shown).

Computer system 400 may implement the techniques described herein using customized hard-wired logic, one or more ASICs or FPGAs, firmware, and/or program logic which in combination with other components of computer system 400 causes or programs computer system 400 to be a special-purpose machine. According to one embodiment, the techniques herein are performed by computer system 400 in response to processor 404 executing one or more sequences of one or more instructions contained in main memory 406. Such instructions may be read into main memory 406 from another storage medium, such as storage device 410. Execution of the sequences of instructions contained in main memory 406 causes processor 404 to perform the process steps described herein. Alternatively or additionally, hard-wired circuitry may be used in place of or in combination with software instructions.

The term "storage media" as used herein refers to one or more non-transitory media storing data and/or instructions that cause a machine to operate in a specific fashion. Such storage media may comprise non-volatile media and/or volatile media. Non-volatile media includes, for example, optical or magnetic disks, such as storage device 410. Volatile media includes dynamic memory, such as main memory 406. Common forms of storage media include, for example, a floppy disk, a flexible disk, hard disk, solid state drive, magnetic tape or other magnetic data storage medium, a CD-ROM or any other optical data storage medium, any physical medium with patterns of holes, a RAM, a programmable read-only memory (PROM), an erasable PROM (EPROM), a FLASH-EPROM, non-volatile random-access memory (NVRAM), any other memory chip or cartridge, content-addressable memory (CAM), and ternary content-addressable memory (TCAM).

A storage medium is distinct from but may be used in conjunction with a transmission medium. Transmission media participate in transferring information between storage media. Examples of transmission media include coaxial cables, copper wire, and fiber optics, including the wires that comprise bus 402. Transmission media may also take the form of acoustic or light waves, such as those generated during radio-wave and infra-red data communications.

Various forms of media may be involved in carrying one or more sequences of one or more instructions to processor 404 for execution. For example, the instructions may initially be carried on a magnetic disk or solid state drive of a remote computer. The remote computer may load the instructions into its dynamic memory and send the instructions over a network, via a network interface controller (NIC), such as an Ethernet controller or Wi-Fi controller. A NIC local to computer system 400 may receive the data from the network and place the data on bus 402. Bus 402 carries the data to main memory 406, from which processor 404 retrieves and executes the instructions. The instructions received by main memory 406 may optionally be stored on storage device 410 either before or after execution by processor 404.

Computer system 400 also includes a communication interface 418 coupled to bus 402. Communication interface 418 provides a two-way data communication coupling to a network link 420 that is connected to a local network 422. For example, communication interface 418 may be an integrated services digital network (ISDN) card, cable modem, satellite modem, or a modem to provide a data communication connection to a corresponding type of telephone line. As another example, communication interface 418 may be a local area network (LAN) card to provide a data communication connection to a compatible LAN. Wireless links may also be implemented. In any such implementation, communication interface 418 sends and receives electrical, electromagnetic or optical signals that carry digital data streams representing various types of information.

Network link 420 typically provides data communication through one or more networks to other data devices. For example, network link 420 may provide a connection through local network 422 to a host computer 424 or to data equipment operated by an Internet Service Provider (ISP) 426. ISP 426 in turn provides data communication services through the world wide packet data communication network now commonly referred to as the "Internet" 428. Local network 422 and Internet 428 both use electrical, electromagnetic or optical signals that carry digital data streams. The signals through the various networks and the signals on network link 420 and through communication interface 418, which carry the digital data to and from computer system 400, are example forms of transmission media.

Computer system 400 can send messages and receive data, including program code, through the network(s), network link 420 and communication interface 418. In the Internet example, a server 430 might transmit a requested code for an application program through Internet 428, ISP 426, local network 422, and communication interface 418.

The received code may be executed by processor 404 as it is received, and/or stored in storage device 410, or other non-volatile storage for later execution.

In an embodiment, a computer network provides connectivity among a set of nodes running software that utilizes techniques as described herein. The nodes may be local to and/or remote from each other. The nodes are connected by a set of links. Examples of links include a coaxial cable, an unshielded twisted cable, a copper cable, an optical fiber, and a virtual link.

A subset of nodes implements the computer network. Examples of such nodes include a switch, a router, a firewall, and a network address translator (NAT). Another subset of nodes uses the computer network. Such nodes (also referred to as "hosts") may execute a client process and/or a server process. A client process makes a request for a computing service (for example, a request to execute a particular application and/or retrieve a particular set of data). A server process responds by executing the requested service and/or returning corresponding data.

A computer network may be a physical network, including physical nodes connected by physical links. A physical node is any digital device. A physical node may be a function-specific hardware device. Examples of function-specific hardware devices include a hardware switch, a hardware router, a hardware firewall, and a hardware NAT. Alternatively or additionally, a physical node may be any physical resource that provides compute power to perform a task, such as one that is configured to execute various virtual machines and/or applications performing respective functions. A physical link is a physical medium connecting two or more physical nodes. Examples of links include a coaxial cable, an unshielded twisted cable, a copper cable, and an optical fiber.

A computer network may be an overlay network. An overlay network is a logical network implemented on top of another network (for example, a physical network). Each node in an overlay network corresponds to a respective node in the underlying network. Accordingly, each node in an overlay network is associated with both an overlay address (to address the overlay node) and an underlay address (to address the underlay node that implements the overlay node). An overlay node may be a digital device and/or a software process (for example, a virtual machine, an application instance, or a thread). A link that connects overlay nodes may be implemented as a tunnel through the underlying network. The overlay nodes at either end of the tunnel may treat the underlying multi-hop path between them as a single logical link. Tunneling is performed through encapsulation and decapsulation.

In an embodiment, a client may be local to and/or remote from a computer network. The client may access the computer network over other computer networks, such as a private network or the Internet. The client may communicate requests to the computer network using a communications protocol, such as Hypertext Transfer Protocol (HTTP). The requests are communicated through an interface, such as a client interface (such as a web browser), a program interface, or an application programming interface (API).

In an embodiment, a computer network provides connectivity between clients and network resources. Network resources include hardware and/or software configured to execute server processes. Examples of network resources include a processor, a data storage, a virtual machine, a container, and/or a software application. Network resources may be shared amongst multiple clients. Clients request computing services from a computer network independently of each other. Network resources are dynamically assigned to the requests and/or clients on an on-demand basis. Network resources assigned to each request and/or client may be scaled up or down based on, for example, (a) the computing services requested by a particular client, (b) the aggregated computing services requested by a particular tenant, and/or (c) the aggregated computing services requested of the computer network. Such a computer network may be referred to as a "cloud network."

In an embodiment, a service provider provides a cloud network to one or more end users. Various service models may be implemented by the cloud network, including but not limited to Software-as-a-Service (SaaS), Platform-as-a-Service (PaaS), and Infrastructure-as-a-Service (IaaS). In SaaS, a service provider provides end users the capability to use the service provider's applications, which are executing on the network resources. In PaaS, the service provider provides end users the capability to deploy custom applications onto the network resources. The custom applications may be created using programming languages, libraries, services, and tools supported by the service provider. In IaaS, the service provider provides end users the capability to provision processing, storage, networks, and other fundamental computing resources provided by the network resources. Any applications, including an operating system, may be deployed on the network resources.

In an embodiment, various deployment models may be implemented by a computer network, including but not limited to a private cloud, a public cloud, and a hybrid cloud. In a private cloud, network resources are provisioned for exclusive use by a particular group of one or more entities (the term "entity" as used herein refers to a corporation, organization, person, or other entity). The network resources may be local to and/or remote from the premises of the particular group of entities. In a public cloud, cloud resources are provisioned for multiple entities that are independent from each other (also referred to as "tenants" or "customers"). In a hybrid cloud, a computer network includes a private cloud and a public cloud. An interface between the private cloud and the public cloud allows for data and application portability. Data stored at the private cloud and data stored at the public cloud may be exchanged through the interface. Applications implemented at the private cloud and applications implemented at the public cloud may have dependencies on each other. A call from an application at the private cloud to an application at the public cloud (and vice versa) may be executed through the interface.

In an embodiment, a system supports multiple tenants. A tenant is a corporation, organization, enterprise, business unit, employee, or other entity that accesses a shared computing resource (for example, a computing resource shared in a public cloud). One tenant (through operation, tenant-specific practices, employees, and/or identification to the external world) may be separate from another tenant. The computer network and the network resources thereof are accessed by clients corresponding to different tenants. Such a computer network may be referred to as a "multi-tenant computer network." Several tenants may use a same particular network resource at different times and/or at the same time. The network resources may be local to and/or remote from the premises of the tenants. Different tenants may demand different network requirements for the computer network. Examples of network requirements include processing speed, amount of data storage, security requirements, performance requirements, throughput requirements, latency requirements, resiliency requirements, Quality of Service (QoS) requirements, tenant isolation, and/or consistency. The same computer network may need to implement different network requirements demanded by different tenants.

In an embodiment, in a multi-tenant computer network, tenant isolation is implemented to ensure that the applications and/or data of different tenants are not shared with each other. Various tenant isolation approaches may be used. In an embodiment, each tenant is associated with a tenant ID. Applications implemented by the computer network are tagged with tenant ID's. Additionally or alternatively, data structures and/or datasets, stored by the computer network, are tagged with tenant ID's. A tenant is permitted access to a particular application, data structure, and/or dataset only if the tenant and the particular application, data structure, and/or dataset are associated with a same tenant ID. As an example, each database implemented by a multi-tenant computer network may be tagged with a tenant ID. Only a tenant associated with the corresponding tenant ID may access data of a particular database. As another example, each entry in a database implemented by a multi-tenant computer network may be tagged with a tenant ID. Only a tenant associated with the corresponding tenant ID may access data of a particular entry. However, the database may be shared by multiple tenants. A subscription list may indicate which tenants have authorization to access which applications. For each application, a list of tenant ID's of tenants authorized to access the application is stored. A tenant is permitted access to a particular application only if the tenant ID of the tenant is included in the subscription list corresponding to the particular application.

In an embodiment, network resources (such as digital devices, virtual machines, application instances, and threads) corresponding to different tenants are isolated to tenant-specific overlay networks maintained by the multi-tenant computer network. As an example, packets from any source device in a tenant overlay network may only be transmitted to other devices within the same tenant overlay network. Encapsulation tunnels may be used to prohibit any transmissions from a source device on a tenant overlay network to devices in other tenant overlay networks. Specifically, the packets, received from the source device, are encapsulated within an outer packet. The outer packet is transmitted from a first encapsulation tunnel endpoint (in communication with the source device in the tenant overlay network) to a second encapsulation tunnel endpoint (in communication with the destination device in the tenant overlay network). The second encapsulation tunnel endpoint decapsulates the outer packet to obtain the original packet transmitted by the source device. The original packet is transmitted from the second encapsulation tunnel endpoint to the destination device in the same particular overlay network.

sequent to the first number of locations by determining locations in the nucleic acid target sequence that match a next-longest subsequence included in the fragment library; and synthesizing, according to the order, the nucleic acid target sequence using a number of fragments from the fragment library.

2. The method of nucleic acid sequence synthesis of claim 1, wherein generating the at least one subsequence catalog comprises the steps of:

---

---

What is claimed is:

1. A method of nucleic acid sequence synthesis, comprising:

providing at least one reference sequence;

determining a plurality of repeated subsequences included in the at least one reference sequence, individual repeated subsequences of the plurality of repeated subsequences including a plurality of bases arranged in a pattern that occurs at multiple locations of the at least one reference sequence;

generating at least one subsequence catalog that includes the plurality of repeated subsequences;

synthesizing a plurality of nucleic acid fragments based on the plurality of repeated subsequences included in the at least one subsequence catalog, the plurality of nucleic acid fragments including at least one nucleic acid fragment for the individual repeated subsequences of the plurality of repeated subsequences;

adding the plurality of nucleic acid fragments to a fragment library;

determining an order for synthesizing a nucleic acid target sequence by:

determining a first number of locations of the nucleic acid target sequence to be synthesized by determining locations of the nucleic acid target sequence that match a longest subsequence included in the fragment library; and determining a second number of locations of the nucleic acid target sequence to be synthesized subi) providing a non-transient computer readable medium encoding the at least one reference sequence and computer-executable code; and ii) returning a subsequence catalog to the same or alternate non-transient computer readable medium;

wherein the computer-executable code is configured to enable a computer processor operably connected to the non-transient computer readable medium to: retrieve the at least one reference sequence; apply at least one pattern-recognition algorithm to the at least one reference sequence to determine the plurality of repeated subsequences; and generate the at least one subsequence catalog.

3. The method of nucleic acid sequence synthesis of claim 2, wherein the at least one pattern-recognition algorithm is a compression algorithm or Lempel-Ziv-Welch compression algorithm.

4. The method of nucleic acid sequence synthesis of claim 2, wherein the alternate non-transient computer readable medium is operably connected with a synthesizer.

5. The method of nucleic acid sequence synthesis of claim 2, comprising:

applying the at least one pattern-recognition algorithm to the at least one reference sequence to determine that at least one repeated subsequence of the plurality of repeated subsequences includes a same pattern of bases repeated two or more times.

6. The method of nucleic acid sequence synthesis of claim 2 further comprising:

subjecting the plurality of repeated subsequences to inclusion criteria;

wherein said inclusion criteria includes at least one of: subsequences that are repeated at least a threshold number of times; subsequences that meet a predetermined threshold number or percentage of repetitions in the at least one reference sequence; subsequences that repeat most frequently; repeating subsequences of at least a minimum number of bases; or subsequences that are not expected to exceed a threshold error rate during synthesis.

7. The method of nucleic acid sequence synthesis of claim 2, further comprising:

iii) providing the at least one subsequence catalog to an assembly planner; and iv) directing, via the assembly planner, the synthesis of the nucleic acid target sequence;

wherein the assembly planner is configured to determine an order of assembly of the nucleic acid target sequence using the at least one subsequence catalog and the plurality of nucleic acid fragments available in the fragment library.

8. The method of nucleic acid sequence synthesis of claim 1, wherein the plurality of nucleic acid fragments include at least two nucleic acids.

9. The method of nucleic acid sequence synthesis of claim 1, wherein the at least one reference sequence is at least two sequences each from a same or a different type.

10. The method of nucleic acid sequence synthesis of claim 1, wherein the nucleic acid target sequence is the same or different from the at least one reference sequence.

11. The method of nucleic acid sequence synthesis of claim 1, wherein the nucleic acid target sequence comprises a non-identical nucleic acid sequence having a same type as the at least one reference sequence.

12. The method of nucleic acid sequence synthesis of claim 1, wherein the nucleic acid target sequence is synthesized according to the order by first synthesizing the first number of locations of the nucleic acid target sequence that correspond to the longest subsequence included in the fragment library and next synthesizing the second number of locations of the nucleic acid target sequence that correspond to the next-longest subsequence in the fragment library.

13. A method of nucleic acid sequence synthesis, comprising:

providing at least one reference sequence;

determining a plurality of repeated subsequences included in the least one reference sequence, individual repeated subsequences of the plurality of repeated subsequences including a plurality of bases arranged in a pattern that occurs at multiple locations of the at least one reference sequence;

generating at least one subsequence catalog that includes the plurality of repeated subsequences;

synthesizing a plurality of nucleic acid fragments based on the plurality of repeated subsequences included in the at least one subsequence catalog, the plurality of nucleic acid fragments including at least one nucleic acid fragment for the individual repeated subsequences of the plurality of repeated subsequences;

adding the plurality of nucleic acid fragments to a fragment library;

determining an order for synthesizing a nucleic acid target sequence by:

determining a first number of locations of the nucleic acid target sequence to be synthesized by determining a longest subsequence included in the fragment library that matches a beginning portion of the nucleic acid target sequence; and determining a second number of locations of the nucleic acid target sequence to be synthesized by determining a next-longest subsequence included in the fragment library that matches a next portion of the nucleic acid target sequence subsequent to the beginning portion; and synthesizing, according to the order, the nucleic acid target sequence using a number of fragments from the fragment library.

14. The method of claim 13, wherein synthesizing the nucleic acid target sequence according to the order includes first synthesizing the longest subsequence included in the fragment library that corresponds to a beginning portion of the nucleic acid target sequence and next synthesizing the next-longest subsequence in the fragment library that corresponds to the next portion of the nucleic acid target sequence.

* * * * *

```
                          SEQUENCE LISTING

<160> NUMBER OF SEQ ID NOS: 2

<210> SEQ ID NO 1
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 1 aatacataa                                                              9

<210> SEQ ID NO 2
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 2
actgaccaat gca                                                        13
```